United States Patent [19]

von Bebenburg et al.

[11] 4,256,752
[45] Mar. 17, 1981

[54] TREATMENT OF ULCERS WITH ACYLATED AMINOALKYL CYANOGUANIDINES CONTAINING A HETEROCYCLIC RESIDUE

[75] Inventors: Walter von Bebenburg, Dreieich; Norbert Schulmeyer, Mörfelden-Walldorf; Istvan Szelenyi, Büttelborn, all of Fed. Rep. of Germany

[73] Assignee: Deutsche Gold- und Silber-Scheideanstalt vormals Roessler, Frankfurt, Fed. Rep. of Germany

[21] Appl. No.: 11,927

[22] Filed: Feb. 13, 1979

[30] Foreign Application Priority Data

Feb. 17, 1978 [GB] United Kingdom ............... 6367/78

[51] Int. Cl.² .................. A61K 31/44; A61K 31/415; C07D 213/58; C07D 233/64
[52] U.S. Cl. ................................. 424/263; 424/250; 424/251; 424/270; 424/272; 424/273 R; 544/224; 544/335; 544/410; 546/291; 546/306; 546/300; 546/330; 548/204; 548/205; 548/214; 548/236; 548/248; 548/301; 548/337; 548/342
[58] Field of Search ............... 548/342, 337, 301; 546/291, 306, 330, 300; 424/273 R, 263

[56] References Cited

U.S. PATENT DOCUMENTS

| | | | |
|---|---|---|---|
| 3,876,647 | 4/1975 | Durant et al. | 546/306 |
| 3,950,333 | 4/1976 | Durant et al. | 424/250 X |
| 3,950,333 | 4/1976 | Durant et al. | 548/337 |
| 3,979,398 | 9/1976 | White | 548/337 |
| 4,060,621 | 11/1977 | Durant et al. | 546/306 |
| 4,098,898 | 7/1978 | Durant et al. | 548/337 |
| 4,112,234 | 9/1978 | Crenshaw et al. | 548/342 |

FOREIGN PATENT DOCUMENTS

| | | | |
|---|---|---|---|
| 2211454 | 10/1972 | Fed. Rep. of Germany | 548/342 |
| 2344779 | 3/1974 | Fed. Rep. of Germany | 548/342 |
| 2389608 | 12/1978 | France . | |

OTHER PUBLICATIONS

Elderfield, Heterocyclic Compounds, vol. 5, pp. 111, 474, 547, 615–616 & 711–712, N.Y., Wiley, 1957.
Hofmann, Imidazole and Its Derivatives Part I, pp. 60 & 61, N.Y., Interscience, 1953.
Klingsberg, Pyridine and Its Derivatives Part Three, pp. 619–620, N. Y., Interscience-Wiley, 1962.
Wiley, et al., Pyrazoles, Pyrazolines, Pyrazolidines, Indazoles and Condensed Rings, p. 126, N.Y., Interscience-Wiley, 1967.
Timmons et al., J. Org. Chem., 1966, vol. 32, pp. 1566–1572.

*Primary Examiner*—Henry R. Jiles
*Assistant Examiner*—Richard A. Schwartz
*Attorney, Agent, or Firm*—Cushman, Darby & Cushman

[57] ABSTRACT

There are prepared compounds corresponding to the formula

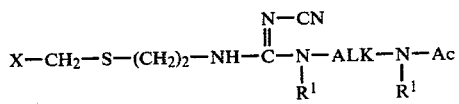

in which X is a 5-membered or 6-membered aromatic heterocyclic radical which is attached through a carbon atom to the adjacent CH₂-group and which contains from 1 to 3 nitrogen atoms or one nitrogen atom and one oxygen or sulphur atom, and which may be substituted once or twice by substituents defined hereinbelow, each $R^1$ represents hydrogen or a $C_1$–$C_4$-alkyl group, Alk represents a $C_2$–$C_6$-alkylene chain and Ac is defined hereinbelow and their salts.

15 Claims, No Drawings

TREATMENT OF ULCERS WITH ACYLATED AMINOALKYL CYANOGUANIDINES CONTAINING A HETEROCYCLIC RESIDUE

BACKGROUND OF THE INVENTION

This invention relates to new acylated aminoalkyl-cyanoguanidines containing a heterocyclic radical.

Compounds corresponding to the general formula:

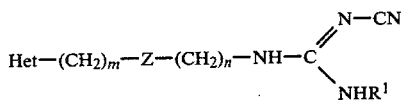

in which $R^1$ represents hydrogen, a $C_1$–$C_4$-alkyl radical or, unless Het is a pyridine ring, may even represent a dialkylaminoalkyl radical, Het is a nitrogen-containing 5-membered or 6-membered heterocyclic radical, Z is a sulphur or oxygen atom, an NH-group or a methylene group and m and n either have the value zero or are integers with a value of from 1 to 4 and the sum of m and n has a value of from 2 to 4, and their salts are already known (cf. German Offenlegungsschrift No. 2,344,779 and German Offenlegungsschrift No. 2,211,454). According to these Offenlegungsschrifts, the known compounds are suitable for inhibiting certain histamine effects by acting on the H2-receptors, and for inhibiting the secretion of stomack acid stimulated by histamine, pentagastrin or even by foods. Reference is also made to antiphlogistic activity.

SUMMARY OF THE INVENTION

The present invention provides new compounds corresponding to the formula:

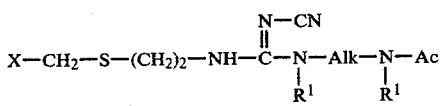

in which X is a 5-membered or 6-membered aromatic heterocyclic radical which is attached through a carbon atom to the adjacent $CH_2$-group and which contains from 1 to 3 nitrogen atoms or one nitrogen atom and one oxygen or sulphur atom and which may be substituted once or twice by halogen atoms, $C_1$–$C_4$-alkyl groups, $C_1$–$C_4$-hydroxyalkyl groups, $C_1$–$C_4$-alkoxy groups, $C_2$–$C_4$-hydroxyalkoxy groups, $C_1$–$C_4$-alkyl mercapto groups, $C_1$–$C_4$-monoalkylamino groups, di-$C_1$–$C_4$-alkylamino groups, hydroxy groups, mercapto groups or amino groups, each $R^1$ represents hydrogen or a $C_1$–$C_4$-alkyl group, Alk represents a $C_2$–$C_6$-alkylene chain and Ac represents a $C_2$–$C_8$-alkanoyl radical or a benzoyl radical respectively substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, sulphamoyl groups, $C_1$–$C_4$-alkylsulphinyl groups or $C_1$–$C_4$-alkylsulphonyl groups, or in which Ac is a cyano group, a formyl group, a $C_2$–$C_6$-alkencarbonyl group, a $C_2$–$C_6$-alkincarbonyl group or such alkenecarbonyl group or alkincarbonyl group substituted by a $C_2$–$C_6$ carbalkoxy group, a $C_3$–$C_6$-cycloalkanocarbonyl group or such a group substituted by halogen and/or a $C_1$–$C_6$ alkyl group, or in which Ac is a $C_1$–$C_6$-alkylsulphonyl radical or a phenyl sulphonyl radical in which the alkyl or phenyl moiety may be substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, $C_1$–$C_4$-alkylsulphinyl groups, $C_1$–$C_4$-alkylsulphonyl groups, sulphamoyl groups, hydroxy groups, mercapto groups, $C_1$–$C_4$-alkoxy groups, $C_1$–$C_4$-alkyl mercapto groups or $C_1$–$C_4$-alkyl groups and their salts.

The heterocyclic radical X is monocyclic and is aromatic in character. For example, X represents an imidazole, pyrazole, pyridine, thiazole, isothiazole, oxazole, isooxazole, pyrimidine, pyrazine, triazole or pyridazine radical. The carbon atom of the radical X which this radical is attached to the rest of the molecule is preferably adjacent a nitrogen atom of the heterocyclic radical X. The radicals in question are, for example, the following heterocyclic radicals: pyridyl-(2), imidazole-(2), imidazolyl-(4), imidazolyl-(5), oxazolyl-(2), oxazolyl-(4), thiazolyl-(2), thiazolyl-(4), issoxazolyl-(3), isothiazolyl-(3), pyrimidyl-(2), pyrimidyl-(4), pyrimidyl-(6), pyrazinyl-(2), pyridazinyl-(3). The substituents of the heterocyclic radical X are preferably situated on the carbon atoms of X. However, they may also be situated on a basic nitrogen atom of X. The radical X is preferably substituted by a $C_1$–$C_4$-alkyl radical, for example the methyl, ethyl, propyl, isopropyl, butyl, isobutyl or tert.-butyl radical. The meanings just mentioned also apply in cases where the substituents of X are monoalkylamino groups, dialkylamino groups or alkyl mercapto groups. Where the radical X contains alkoxy groups, the alkoxy groups in question are preferably methoxy or ethoxy groups but can also be propoxy or butoxy. Where X contains halogen atoms, the halogen atoms in question are, for example, chlorine, fluorine or bromine. When X contains a hydroxy group it can be, for example, hydroxymethyl hydroxyethyl, hydroxypropyl or hydroxybutyl. When X contains a $C_2$–$C_4$-hydroxyalkoxy group it can be, for example, hydroxyethyl, hydroxypropoxy or hydroxybutoxy. When X contains a $C_1$–$C_4$-alkyl mercapto group it can be, for example, methylthio, ethylthio, propylthio, butylthio, or t-butylthio. When X contains a $C_1$–$C_4$-monoalkylamino or di-$C_1$–$C_5$-alkylamino group it can be, for example, methylamino, ethylamino, propylamino, butylamino, isopropylamino, dimethylamino, diethylamino, dipropylamino, dibutylamino, di sec. butylamino or methyl ethyl amino.

Where Ac is an alkanoyl radical, the alkanoyl radical in question may be linear or branched (for example acetyl, propionyl, isopropionyl, butyryl, pentanoyl). Substituents of the alkanoyl radical are preferably situated in the α-position to the —CO—group, the substituents in question being identical or different ones of those mentioned above. The benzoyl radical is preferably substituted in the o- and/or p-position. Where the radical Ac is substituted by halogen atoms, the halogen atoms in question are, for example, fluorine, chlorine or, optionally, even bromine. Alkyl radicals as such or as part of other groups (for example carbalkoxy, alkylcarbonyl, alkoxy) may be linear or branched.

Ac can be a $C_2$–$C_8$-alkanoyl radical or a benzoyl radical respectively substituted once, twice or three times by halogen atoms, nitrile groups, nitro groups, carboxy groups, carbamoyl groups, $C_2$–$C_5$-alkylcarbonyl groups, $C_2$–$C_5$ carbalkoxy groups or $C_1$–$C_4$-alkylsulphonyl groups, or in which Ac is a $C_1$–$C_6$-alkylsulphonyl radical or a phenyl sulphonyl radical in which the alkyl or phenyl moiety may be substituted once, twice, or three times by halogen atoms, nitrile groups, carboxy groups, carbamoyl groups, $C_2$–$C_5$-alkylcarbonyl groups, $C_2$–$C_5$-carbalkoxy groups, $C_3$–$C_4$-alkylsulphinyl groups, $C_1$–$C_4$-alkylsulphonyl groups, sulphamoyl groups, hydroxy groups, mercapto groups, $C_1$–$C_4$-alkoxy groups, $C_1$–$C_4$-alkyl mercapto groups or $C_1$–$C_4$-alkyl groups. Ac can also be a $C_2$–$C_8$-alkanoyl group substituted by a $C_2$–$C_5$-carbalkoxy group, a cyano group, 1 to 3 halogen atoms, a $C_1$–$C_4$-alkyl sulphinyl group, a $C_1$–$C_4$-alkyl sulphonyl group, a $C_2$–$C_5$-alkylcarbonyl group or Ac is a lower alkylphenyl sulphonyl radical or a halophenylsulphonyl radical. Ac can also be carbomethoxyacetyl, cyanoacetyl, trifuloroacetyl, monofluoroacetyl, 2-cyanopropionyl, dichloroacetyl, 2-cyanocaproyl, 2-cyanisobutyl, methylsulphinylacetyl, methylsulphonylacetyl, methylsulphonyl, methylcarbonylacetyl, tolylsulphonyl, chlorophenylsulphonyl or trichloroacetyl. Ac can also be lower alkoxyethinyl carbonyl or cyclopropyl carbonyl or cyclopropyl carbonyl substituted with at least one lower alkyl or halogen or both lower alkyl and halogen. When Ac is cyclopropane carbonyl it can have 0 to 3 methyl or chloro substituents.

$R^1$ is for example hydrogen, a methyl, ethyl, propyl, isopropyl, butyl, isobutyl or tert.-butyl radical and is preferably hydrogen or the methyl group.

The alkylene chain Alk may be linear or branched, examples being —$(CH_2)_2$—, —$(CH_2)_3$—, —$(CH_2)_4$—, —$(CH_2)_5$—, —$(CH_2)_6$—, —$CH(CH_3)$—$CH_2$—, —$CH(CH_3)$—$(CH_2)_2$. Alk can be a $C_2$–$C_3$ alkylene group.

More particularly, the symbol Ac represent an acetyl propionyl, butyryl, pentanoyl, hexanoyl, heptanoyl or octanoyl radical substituted in the α-position by one ot two chlorine atoms or by one or two bromine atoms or by a cyano group, a carboxy group, a carbamoyl group, a carbomethoxy group, a carboethoxy group, a carbopropoxy group, a carboamyloxy group, a propionyl group, a butyryl group, a valeoryl group, a sulphamoyl group, a methyl sulphinyl group, an ethyl sulphinyl group, a butyl sulphinyl group, a methyl sulphonyl group, an acetyl group, a cyano group, a formyl group, a $C_2$–$C_6$ alkencarbonyl group, e.g., vinyl carbonyl, allyl carbonyl butenyl carbonyl, acetylene carbonyl, vinyl carbonyl substituted by carbomethoxy or carboethoxy, a $C_3$–$C_6$ cycloalkancarbonyl or such a group substituted by halogen or a $C_1$–$C_6$ alkyl group, for example, cyclopropane-carbonyl, cyclopentane carbonyl, cyclohexane carbonyl, 2-chloro-cyclopropyl, 2,3-dichlorochloropropyl, 2-chlorocyloahexyl, 2-bromocyclobutyl, 4-chlorocyclohexyl, 2-methylcoclopropyl, 2,3-dimethylcyclohexyl, 2-ethylcyclohexyl, 2-methylcoclohexyl, 4-methylcyclohexyl, 2-hexycyclopropyl. The following radicals are examples of Ac: chloroacetyl, acetyl, fluroracetyl, difluoroacetyl, cyanoacetyl, α-cyanopropyl, α-cyanoheptamoyl, α-cyanooctanoyl, nitroacetyl, α-nitrobutyryl, carboxyacetyl, carboethoxyacetyl, carbamoylacetyl, acetoacetyl methyl sulphonylacetyl, methyl sulphinylacetyl, ($CH_3$—$SO$—$CH_2$—$CO$—).

In the case of the acetyl radical, the trichloroacetyl and trifluoroacetyl radicals are also suitable.

Where Ac is the substituted benzoyl radical, the benzoyl radical in question is in particular a chlorobenzoyl radical, a fluorobenzoyl radical, a cyanobenzoyl radical, a carboxybenzoyl radical, a carbamoyl benzoyl radical, an acetylbenzoyl radical, a carbomethoxybenzoyl radical, a carbeothoxybenzoyl radical, a carboamyloxy group, a supphamoylbenzoyl radical, a methylsulphinylbenzoyl radical or a methylsulphonylbenzoyl radical, these substituents being situated in the o- or p- position or in the o- and p-positions. The following radicals are examples of this radical; -chlorobenzoyl, p-cyanobenzoyl, p-methylsulphonylbenzoyl, p-sulphamoylbenzoyl ($CO$—$C_6H_4$—$SO_2$—$NH_2$).

In addition, Ac preferably represents a methylsulphonyl ($CH_3$—$SO_2$—), ethylsulphonyl, propylsulphonyl or butylsulphonyl radical or a phenylsulphonyl radical, the latter optionally being substituted by one or two chlorine atoms, by one or two fluorine atoms or by one or two methyl groups, preferably in the o- and/or p-position. Examples of these radicals are methylsulphonyl, ethylsulphonyl, phenylsulphonyl, p-tolyl sulphonyl, p-chlorophenylsulphonyl (p—Cl—$C_6$—$H_4$—$SO_2$—).

The compounds according to the invention show pharmacodynamic activity. For example, they inhibit stomach secretion, particularly the secretion of stomach acid, and show strong antihistamine activity of the "$H_2$-blocker" type. In addition, they have an ulcer-healing effect.

Accordingly, an object of the present invention is to provide compounds with favourable pharmacodynamic properties which may be used as medicaments.

The effect of the compounds according to the invention is suprising in view of the already known compounds because, of the already known compounds, only those corresponding to the formula

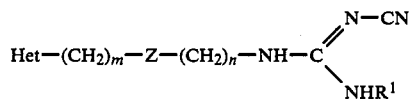

in which $R^1$ is a methyl group, show any significant pharmacological activity. The mere replacement of the methyl group by an ethyl group is sufficient to produce a considerable loss of activity. Compounds where $R^1$ in the last formula is a dialkylaminoalkyl group (German Offenlegungsschrift No. 2,211,454) are also ineffectural.

The present invention also provides a process for the production of compounds of formula I as defined above, wherein (a) a compound corresponding to the formula:

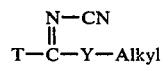  II in which Y is an oxygen or sulphur atom and alkyl is a saturated $C_1$–$C_6$-alkyl radical, is reacted with a compound corresponding to the formula:

H—U  III

T and U in formulae II and III being different from one another, one representing the group X—$CH_2$—S—$(CH_2)_2$—NH— and the other representing the group —$NR^1$—Alk—$NR^1Ac$, and the products of this reaction are optionally alkylated, or (b) a compound corresponding to the formula:

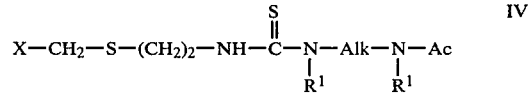  IV is reacted with a heavy metal salt of cyanamide and the reaction products are optionally alkylated, or (c) a compound corresponding to the formula

     V)

is reacted with a compound corresponding to the formula:

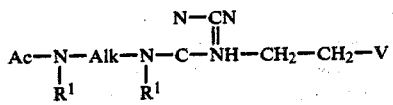     VI

V and W in formulae V and VI are different from one another one representing the group -SH and the other representing the group Z, where Z represents a hydroxy group which may even be esterified by a strong inorganic or organic acid or represents an alkoxy or aryloxy group, and the products of this reaction are optionally alkylated, or (d) a compound corresponding to the formula:

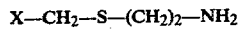     VII is reacted with a compound corresponding to the formula:

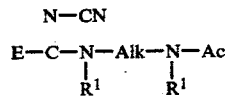     VIII in which E represents an amino group, which may also contain a protective acyl group, or represents a $C_1-C_6$-alkoxy group or a $C_1-C_6$-alkyl thio group, or in which E and the group $-NR^1-Alk-NR^1Ac$ together may also form the group $=N-Alk-N-R^1Ac$, and the products of this reaction are optionally alkylated, or (e) a compound corresponding to the formula:

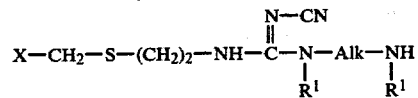     IX is reacted with a compound AcB where Ac is defined above and B represents a hydroxy groups, bromine, chlorine, iodine, a $C_1-C_6$-alkoxy group, a $C_1-C_6$-alkylmercapto group, a $C_1-C_6$-alkylcarbonyloxy group, the group AcO-; an amino, $C_1-C_6$-alkylamino or di-$C_1-C_6$-alkylamino group or the imidazolyl-(1)-radical, and the products of this reaction are optionally alkylated.

Method (a) is carried out for example in a polar solvent such as water, methanol, ethanol, isopropanol, dimethyl formamide, dimethyl sulphoxide, acetonitrile or even excess amine, at a temperature of from −20° to +200° C. and preferably at a temperature of from 50° to 150° C. in the presence or absence of base (alkali metal hydroxide, e.g. sodium hydroxide or potassium hydroxide). When volatile amines are used, the reaction has to be carried out in a closed system, optionally under pressure (for example up to 100 bars).

The starting materials for this method are known or are obtained by methods similar to those described in German Offenlegungsschrift Nos. 2,211,454 and 2,344,779. The entire disclosure of these two German Offenlegungsschrifts is hereby incorporated by reference and relied upon.

For example, a compound corresponding to general formula III, namely 2-aminoethyl mercaptomethyl pyridine, is obtained as follows:

80 g of α-pyridyl carbinol are boiled under reflux for 24 hours with 120 g of cysteamine hydrochloride in 620 ml of 43% hydrobromic acid. The mixture is concentrated by evaporation in vacuo and the residue is recrystallised from methanol, giving 202 g of the dihydrobromide of the above mentioned compound melting at 188° to 189° C.

The cysteamine used for this reaction may even be replaced by cysteamine derivatives which, on the nitrogen atom, carry a protective group that is eliminated on completion of the reaction. For example, mercaptoethyl phthalidmide may be reacted with picolyl chloride under alkaline conditions and the reaction product may be reacted-optionally without isolation-with mineral acids or hydrazine with elimination of the protective group to form 2-aminoethyl mercaptomethyl pyridine.

A compound of formula II, for example N-cyano-N'-2-[pyridyl-(2)-methylthio]-ethyl-S-methylisothiourea, is obtained as follows:

A solution of 14 g of NaOH in 30 ml of water is added to a mixture of 54 g of 2-aminoethyl mercaptomethyl pyridine (dihydrobromide) and 200 ml of ethanol. 22 g of cyanamidodithiocarbonic acid dimethyl ester, (Timmons J. Org. Chem. 32 (1967), pages 1566-1572 at pages 1569) are added to the clear solution thus formed which is then stirred for 3 hours at 30° C., methyl mercaptan being given off. 1 liter of water is then added and, after stirring for 30 minutes, the crystals precipitated are filtered off under suction. They are washed with water (yield: 31 g, m.p.: 82°-84° C.).

Starting materials of formula II, in which T represents group $-NR^1-Alk-NR^1-Ac$, are similarly obtained for example by reacting the corresponding amine, $HNR^1-Alk-NR^1Ac$, with cyanamide-dithiocarbonic acid dimethyl ester.

Amines corresponding to the formula $HNR^1-Alk-NR^1Ac$ may be obtained by reacting compounds corresponding to the formula $HNR^1-AlkNR^1H$, in which an amine moiety is optionally protected by one of the usual, readily removable protective groups, with a compound AcB in which Ac is as defined above and B is a hydroxy group, bromine, chlorine, iodine, a $C_1-C_6$-alkoxy group, a $C_1-C_6$-alkylmercapto group, a $C_1-C_6$-alkyl carbonyloxy group, the group AcO, an amino, $C_1-C_6$-alkylamino or di $C_1-C_6$-alkylamino group or the imidazolyl-(1)-radical, in an inert solvent lower alcohols, e.g. methanol, ethanol, isopropanol, dioxane, dimethyl formamide, lower chlorinated hydrocarbons, toluene or mixtures thereof with water at a temperature in the range from 0° to 200° C., preferably at a temperature in the range from 20° to 150° C., and optionally in the presence of an acid-binding agent. Any protective group present is then removed in the usual way. The protective group used in this cay may even be inter alia a protective group of the type which can be removed by hydrogenation, such as for example, a benzyl group or a carbobenzoxy radical.

Illustrative of additional compounds of formula III which can be used in the present invention are:
imidazolyl-(4)-methylthioethylamine,
5-methyl-imidzolyl-(4)-methylthioethylamine,
5-ethyl-imidazolyl-(4)-methylthioethylamine,
5-butyl-imidazolyl-(4)-methylthioethylamine, 2,5-dimethyl-imidazolyl-(4)-methylthioethylamine,
1-methyl-imidazolyl-(4)-methylthioethylamine,
5-chloro-imidazolyl-(4)-methylthioethylamine,
2,5-dichloro-imidazolyl-(4)-methylthioethylamine,
5-fluoro-imidazolyl-(4)-methylthioethylamine,
5-bromo-imidazolyl-(4)-methylthioethylamine,
5-hydroxyethyl-imidazolyl-(4)-methylthioethylamine,
5-hydroxymethyl-imidazolyl-(4)-methylthioethylamine,
5-hydroxymethyl-imidazolyl-(4)-methylthioethylamine,
5-hydroxybutyl-imidazolyl-(4)-methylthioethylamine,
5-methoxy-imidazolyl-(4)-methylthioethylamine,
5-butoxy-imidazolyl-(4)-methylthioethylamine,
5-hydroxyethoxy-imidazolyl-(4)-methylthioethylamine,
5-hydroxybutoxy-imidazolyl-(4)-methylthioethylamine,
5-methylmercapto-imidazolyl-(4)-methylthioethylamine,
5-butylmercapto-imidazolyl-(4)-methylthioethylamine,
5-methylamino-imidazolyl-(4)-methylthioethylamine,
5-butylamino-imidazolyl-(4)-methylthioethylamine,
5-diethylamine-imidazolyl-(4)-methylioethylamine,
5-methyl butyl amino-imidazolyl-(4)-methylthioethylamine,
5-hydroxy-imidazolyl-(4)-methylthioethylamine,
5-mercapto-imidazolyl-(4)-methylthioethylamine,
5-amino-imidazolyl-(4)-methylthioethylamine,
5-methyl-imidazolyl-(2)-methylthioethylamine,
2-methyl-imidazolyl-(5)-methylthioethylamine,
3-chloro-pyridyl-(2)-methylthioethylamine,
pyrazolyl-(3)-methylthioethylamine,
5-methyl pyrazolyl-(3)-methylthioethylamine,
3-methyl pyrazolyl-(5)-methylthioethylamine,
5-methyl triazolyl-(4)-methylthioethylamine,
4-methyl triazolyl-(5)-methylthioethylamine,
4-methyl-oxazolyl-(2)-methylthioethylamine,
2-methyl-oxazolyl-(4)-methylthioethylamine,
4-methyl-thiazolyl-(2)-methylthioethylamine,
2-methyl-thiazolyl-(4)-methylthioethylamine,
isoxazolyl-(3)-methylthioethylamine,
isothiazolyl-(3)-methylthioethylamine,
4-methyl-pyrimidyl-(2)-methylthioethylamine,
6-methyl-pyrimidyl-(4)-methylthioethylamine,
2-methyl-pyrimidyl-(6)-methylthioethylamine,
3-methyl-pyrazinyl-(2)-methylthioethylamine, and
4-methyl-pyridazinyl-(3)-methylthioethylamine.

Any of the heterocyclic compounds just mentioned can be reacted for example with a compound of formula II, where T is $NR^1$—Alk—$NR^1AC$, e.g. 2-carbmethoxyacetylaminoethyl-S-methyl-N-cyano isothiourea, using the procedured of German OS No. 2,344,779, Example 1 for example. Ac can also be any of the Ac groups set forth above.

Method (b):

Method (b) is carried out for example in a polar solvent, such as dimethyl formamide, dimethyl sulphoxide or acetonitrile, with a large excess of the heavy metal salt at a temperature of from 50° to 200° C. and preferably at a temperature of from 70° to 160° C. The heavy metal salts used are, for example, lead, mercury or cadmium salts. The thiourea corresponding to general formula IV may even be initially desulphurised with a heavy metal salt or oxide and then reacted with cyanamide.

The starting materials for this process are known or are obtained by methods similar to those described in German Offenlegungsschrifts No. 2,211,454 and No. 2,344,779.

In the resulting compounds which correspond to the formula X—$CH_2$—S—$(CH_2)_2$—NH—CS—$NH_2$, the group —Alk—$NR^1$Ac for example is subsequently obtained by reaction in the usual way with a compound corresponding to the formula Hal—Alk—$NR^1$Ac (Hal=Cl or Br) in an inert solvent, optionally in the presence of base, at a temperature of from 30° to 200° C.

Method (c):

Method (c) is carried out for example in an aqueous or aqueous-alcoholic mineral acid, such as hydrochloric or hydrobromic acid, or in an alcoholic solution containing added base, such as alkali metal carbonate (potassium carbonate), alkali metal hydroxide (sodium hydroxide), tertiary amine (triethylamine) and the like, or in an inert solvent, such as ether, dioxane, tetrahydrofuran and so on, with addition of boron trifluoride. The reaction temperature is for example in the range from −20° to +150° C. and preferably in the range from 30° to 120° C.

Where Z is an esterified hydroxy group, the ester in question is a reactive ester. In this context, a reactive ester is for example the ester of a strong organic or inorganic acid. In this case, Z is for example a halogen atom such a chlorine, bromine or iodine, or the group —$OSO_2$ OAlk or —$OSO_2$OAr, where Alk is a lower alkyl group e.g., methyl, ethyl, propyl or butyl and Ar is a phenyl or naphthyl radical optionally substituted by lower alkyl radicals, for example the p-toluene sulphonyl radical. Where a reactive ester is used, the reaction is advantageously carried out in the presence of a basic condensation agent.

Where Z is an alkoxy group, the alkoxy group in question is for example a lower aliphatic linear or branched alkoxy group containing from 1 to 6 carbon atoms, e.g., methoxy, ethoxy, hexoxy.

Where Z is an aryloxy group, the aryloxy group in question is for example a phenoxy group, the phenyl radical optionally being substituted by lower alkyl radicals, e.g., methyl, ethyl propyl, butyl, halogen atoms, e.g., chlorine or bromine nitro groups or cyano groups.

The starting materials for method (c) may be obtained for example as follows:

The reaction of a compound corresponding to formula V, in which W represent chlorine, bromine, iodine or an alkane sulphonyloxy radical, with sodium hydrogen sulphide, alkanols, phenols, or benzyl alcohol or with the corresponding metal salts thereof in polar solvents, such as alcohols e.g., methyl alcohol, ethyl alcohol, dimethyl formamide, dimethyl sulphoxide, dioxane, acetonitrile, glycols, e.g. ethylene glycol, propylene glycol, polyglycol ethers, polyglycol ethers, gives for example compounds corresponding to formula V in which W is a mercapto group or an e.g. methoxy, or aryloxy, e.g. phenoxy group. Instead of using sodium hydrogen sulphide, it is also possible to use an alkali metal salt (potassium salt) of thioacetic acid and subsequently to remove the acetyl group by heating with a mineral acid.

Compounds of formula VI may be produced for example as follows:

A cyanamido-dithiocarbonic acid dialkyl ester, e.g., the dimethyl ester or diethyl ester is reacted with an amine $HNR^1$-Alk-$NR^1$Ac in the usual way (in a polar solvent such as an alcohol, e.g., ethyl alcohol, dimethyl formamide, water; 0°–100° C. with elimination of 1 mole of alkyl mercaptan, and the compound thus obtained is reacted with a compound of the formula $H_2N$—$CH_2$—$CH_2$—V under similar conditions with elimination of the second mole of alkyl mercaptan.

For the production of amines corresponding to the formula NHR¹—Alk—NR¹Ac, see method (b).

Method (d):

Method (d) may be carried out in solution or in the melt at a temperature of from 20° to 150° C., optionally under elevated pressure. Suitable solvents are for example, water or organic solvents, such as alcohols, e.g. ethyl alcohol, toluene, xylene, dioxane, alcohol-water mixtures. The compounds of formula VIII may be used in the form of the free base or even in the form of the usual acid addition salts. If, in formula VIII, E and the group NR¹-Alk-NR¹Ac together form the group =N—Alk—NR¹Ac, the compounds in question are diimides corresponding to the formula:

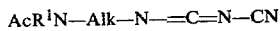

Starting materials of formula VIII for method (d) are obtained for example by reacting 1 mole of a cyanamidodithiocarbonic acid dialkyl ester in a polar solvent (alcohols, water, dimethyl formamide) at 0° to 150° C. with 1 mole of amine HNR¹—Alk—NR¹Ac with elimination of 1 mole of alkyl mercaptan, and optionally replacing the radical E in the resulting compound by an amino group or an alkoxy group (reaction with ammonia or a lower alcohol under the above-mentioned conditions).

For the production of amines corresponding to the formula HNR¹—Alk—NR¹Ac, see method (a).

Method (e):

Acylation may be carried out in an inert solvent or suspending agent, such as a lower alcohol (methanol, ethanol), dioxane, dimethyl formamide, benzene, toluene, a lower chlorinated hydrocarbon, e.g., methylene chloride, chloroform, or a mixture thereof with water (alcohol/H₂O-mixtures; H₂O/toluene; H₂O/CH₂Cl₂; H₂O/CHCl₃), at a temperature of from 0° to 200° C. and preferably at a temperature of from 20° to 150° C. The reaction is optionally carried out in the presence of an acid-binding agent, such as an alkali metal carbonate e.g., sodium carbonate, an alkali metal hydroxide, e.g., sodium or potassium hydroxide, an alkali metal alcoholate e.g., sodium ethylate, or a tertiary amine, for example triethylamine. It is even possible initially to prepare a corresponding alkali metal compound of the compound IX to be reacted by reacting it with an alkali metal, alkali metal hydride, or alkali metal amide (particularly sodium or sodium compounds) in an inert solvent, such as dioxane, dimethyl formamide, benzene or toluene, at a temperature of from 0° C. to 150° C. and subsequently adding the acylating agent.

The acylating agent may even be used in excess. Where acylation is directly carried out with an acid AcOh, it is of advantage and in some cases even necessary to add corresponding condensation agents such as, for example dicyclohexyl carbodiimide or 1-methyl-2-ethoxycarbonyl dihydroquinoline.

The starting compounds for method (e) are obtained for example from the known compounds corresponding to the formula:

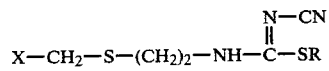

(R=a lower alkyl radical, e.g., methyl or ethyl) by reaction with a diamine corresponding to the formula HNR¹—Alk—NR¹H in a polar solvent (H₂O, lower alcohols, dimethyl formamide, dimethyl sulphoxide, acetonitrile or even excess amine) at a temperature of from −20° to 200° C. and preferably at a temperature of from 50° to 150° C., optionally in the presence of base (alkali metal hydroxides). The end products of formula I are obtained either in free form or in the form of their salts, depending upon the process conditions applied and the starting materials used. The salts of the end products may be converted back into the bases in known manner, for example with alkali or ion exchangers. Salts can be obtained from the bases by reaction with organic or inorganic acids, particularly those of the type which are suitable for forming therapeutically compatible salts. Acids of this type are, for example, hydrohalic acids, e.g. hydrochloric acid, hydrobromic acid, sulphuric acid, phosphoric acids, nitric acid, perchloric acid, organic mono-, di- or tri-carboxylic acids of the aliphatic, alicyclic, aromatic or heterocyclic series, and also sulphonic acids. Examples of acids such as these are formic acid, acetic acid, propionic acid, succinic acid, glycolic acid, lactic acid, malic acid, tartaric acid, citric acid, ascorbic, acid, maleic acid, fumaric acid, hydroxy maleic acid or pyruvic acid; phenyl acetic acid, benzoic acid, salicylic acid or p-aminobenzoic acid, anthranilic acid, p-hydroxy benzoic acid, salicylic acid or p-aminosalicylic acid, embonic acid, methane sulphonic acid, ethane sulphonic acid, hydroxyethane sulphonic acid, ethylene sulphonic acid, e.g. p-toluene sulfonic acid, naphthalene sulphonic acid or sulphanilic acid or even 8-chlorotheophylline.

In the above-described methods for producing the compounds according to the invention, amino, hydroxy or mercapto groups which are present in the starting substances, but which do not take any part in the reaction, may contain known protective groups of the usual type. The protective groups in question are in particular radicals which can readily be removed by hydrolysis and which may even be removed during the reaction itself. Where protective groups of this type are not removed during the reaction, they are eliminated after the reaction. In many cases, the starting compounds already contain protective groups of the type in question from their production. In this case, the protective groups are, for example, acyl groups which can readily be removed by solvolysis. Protective groups such as these are removed for example by hydrolysis with dilute acids or by means of bases (potash, soda, aqueous alkali solutions, alcoholic alkali solutions, NH₃) at a temperature of from 20° to 100° C.

Examples of radicals such as these, i.e. radicals which can be removed by hydrolysis, are the trifluoroacetyl radical, the phthalyl radical, the trityl radical, the p-toluene sulphonyl radical and the like, and also lower alkanoyl radicals, such as the acetyl radical, the formyl radical, the tert.-butyl carboxy radical and the like. In particular, it is also possible to use the protective groups normally encountered in the synthesis of peptides and to remove them by the methods normally used there. In this connection, reference is also made inter alia to the book by Jesse P. Greenstein and Milton Winitz entitled "Chemistry of Amino Acids", N.Y. 1961, John Wiley and Sons, Inc., Volume 2, for example pages 883 et seq. It would also be possible to use a carbalkoxy group (for example of low molecular weight), a carbobenzoxy group or a phenoxy carbonyl group.

If necessary, the end products obtained by the methods described above may be alkylated. To this end, the radical R¹ (C₁-C₄-alkyl group) is introduced into compounds of formula I, in which one or both radicals $R^1$ represent hydrogen, or one or more $C_1$-$C_4$-alkyl groups or a $C_2$-$C_4$-hydroxyalkyl group is introduced into compounds of formula I where X contains free hydroxy, mercapto or amino groups. These alkylating reactions are carried out in known manner. Suitable alkylating agents are, for example, $C_1$-$C_4$-diazo alkanes, $C_2$-$C_6$-olefin oxides with an epoxide ring in the $\alpha,\beta$-position, and esters of the formula $R^{1'}$Hal, $ArSO_2OR^{1'}$ and $SO_2$-$(OR^{1'})_2$ hwere Hal is a halogen atom, (particularly chlorine, bromine or iodine) and Ar is an aromatic radical such as, for example, a phenyl or naphthyl radical optionally substituted by one or more lower alkyl radicals, and $R^{1'}$ is a $C_1$-$C_4$-alkyl group or a $C_2$-$C_4$-hydroxyalkyl group. Examples are p-toluene sulphonic acid $C_1$-$C_6$-alkyl ester, lower $C_1$-$C_6$-dialkyl sulphates, ethylene oxide, propylene oxide, $\alpha$-butylene oxide and the like. The alkylating reaction is optionally carried out in the presence of the usual acid binding agents, such as alkali metal carbonates, pyridine or other usual tertiary amines, at a temperature of from 0° to 150° C. in an inert solvent, such as an alcohols, an aliphatic ether, dioxane, tetrahydrofuran, dimethyl formamide, dimethyl sulphoxide, an aromatic hydrocarbon, such as benzene, toluene or acetone.

Alkylation may even be carried out by initially preparing an alkali metal compound of the compound to be alkylated by reacting it with an alkali metal, alkali metal hydride or alkali metal amine (particularly sodium or sodium compounds) in an inert solvent, such as dioxane, dimethyl formamide, benzene or toluene at a temperature of from 0° to 150° C., and subsequently adding the alkylating agent.

The compounds according to the invention are suitable for the production of pharmaceutical compositions and preparations. The pharmaceutical compositions or medicaments contain, as active principle, one or more of the compound according to the invention, optionally in admixture with other pharmacologically or pahrmaceutically active substances. The medicaments may be prepared with the usual pharmaceutical carriers, and diluents.

As carriers and assistants, for example, are those recommended in the following literature as adjuvants for pharmacy, cosmetic and related fields such as in Ullmann's Encyklopädie der technischer Chemie, Vol. 4 (1953), pages 1 to 39; Journal of Pharmaceutical Sciences 52 (1963), pages 918 et seq.; N.Y. Czetsch-Lindenwald, Hilftstoffe für Pharmazie und angrenzende Begiete; Phar. Ind. 2 (1961), pages 72 et seq.; Dr. H. P. Fiedler, Lexicon der Hilftstoffe für Pharmazie, Cosmetik und angrenzende Gebiete, Cantor kg. Aulendorf i. Wurtt (1971).

Examples of such materials include gelatin, natural sugars such as sucrose or lactose, lecithin, pectin, starch (for example cornstarch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose, stearates, e.g., methyl stearate and glyceryl stearate, magnesium and calcium salts of fatty acids with 12 to 22 carbon atoms, especially saturated acids (for example calcium stearate, calcium laurate, magnesium stearate), emulsifiers, oils and fats, especially of plant origin (for example peanut oil, wheat oil, olive oil, sesame oil, cod-liver oil), mono- di- and triglycerides of saturated fatty acids ($c_{12}H_{24}O_2$ to $C_{18}H_{36}O_2$ and their mixtures), e.g., glyceryl monostearate, glyceryl distearate, glyceryl tristearate, glyceryl triluarate), pharmaceitically compatible mono or polyvalent alcohols and polyglycols such as glycerine, mannitol, sobitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms, with monohydric aliphatic alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl acetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water of physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetin, diacetin, glyceryl monostearate, glyceryl distearate, glyceryl monopalmitate, paraffins and the like.

In the production of the preparations there can be used known and customary solution aids or emulsifiers. As solution acid and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives, stabilizers, buffers, for example, calcium hydrogen phosphate, colloidal aluminum hydroxide, taste correctives, antioxidants and complex formers (for example ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metal bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester) benzoic acid, sodium benzoate, trichloroisobutyl alcohol, phenol cresol, benzethodium chloride and formalin derivatives.

The pharmacological and galenical treatment of the compounds of the invention takes place according to the usual standard methods. For example, the active material or materials and assistants or carriers are well mixed by stirring or homogenization (for example by means of a colloid mill or ball mill), wherein the operation is generally carried out at temperatures between 20° and 80° C., preferably 20° and 50° C.

The application of active material or drug can take place on the skin or mucuous membrane or internally, for example, orally, enterally, pulmonally, rectally, intravenously, nasally, vaginally, lingually, intraarterially, intraacardially, intracutaneously, intramuscularly, intraperitoneally, or subcutaneously.

The addition of other medicines is also possible.

The compounds of the invention on perfused stomach lumen rats show a good acid secretion arresting activity. For example in the above mentioned test methods there is produced the stated activity at a dosage of 10 mg/kg of body weight (kg rat) by mouth.

This acid secretion arresting activity is comparable with the action of the known medicine Cimetidine.

The lowest effective dosage in the above mentioned animal experiment is for example 10 mg/kg orally, 5 mg/kg sublingually and 1 mg/kg intravenously.

As the general dosage range for the activity (animal experiments as above) there can be used for example 10 to 20 mg/kg orally; 1 to 10 mg/kg, intravenously and 5 to 10 mg/kg sublingually.

The compounds of the invention are indicated for use in ulcus ventriculi, ulcus duodeni, hyperacidity, Zollinger-Ellison syndrome, and reflux aesophagitis.

The pharmaceutical preparations generally contain between 250 to 500 mg of the active component or components of the invention.

The compounds can be delivered in the form of tablets, capsules, pills, dragees, plugs, salves, gels, creams, powders, dusts, aerosols or in liquid form. As liquid forms there can be used for example oily or alcoholic or aqueous solutions as well as suspension and emulsions. The preferred forms of use are tablets which contain between 250 and 500 mg or solutions which contain between 12.5 and 25% of active material.

In individual doses the amount of active component of the invention can be used for example in an amount of:

a. in oral dispensation between 250 and 500 mg;
b. in parenteral dispensation (for example intravenously, intramuscularly) between 250 and 500 mg.

The dosages in each case are based on the free base.

For example, there is recommended the use of 1 to 2 tablets containing 250 to 500 mg of active ingredient 3 times daily or for example, intravenously the injection 1 to 3 times daily of a 2 to 4 ml ampoule containing 250 to 500 mg of active dosage. In oral administration, the minimum daily dosage is for example 500 mg; the maximum daily dosage in oral administration should not be over 5000 mg.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is above 12,000 mg/kg, in intravenous application above 725 mg/kg.

The drugs can be used in human medicine, in veterinary medicine as well as in agriculture alone or in admixture with other pharmacologically active materials. The compounds can be used to treat dogs and cats.

The compositions can comprise, consist essentially of or consist of the materials set forth.

The methods can comprise, consist essentially of or consist of the steps set forth with the materials shown.

Unless otherwise indicated all parts and percentages are by weight.

DESCRIPTION OF THE PREFERRED EMBODIMENTS

EXAMPLE 1

N-Cyano-N'-[2-carbmethoxyacetylamino-ethyl]-N''-(2-[5-methylimidazolyl-(4)-methylthio]-ethyl)-guanidine

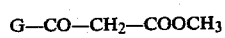

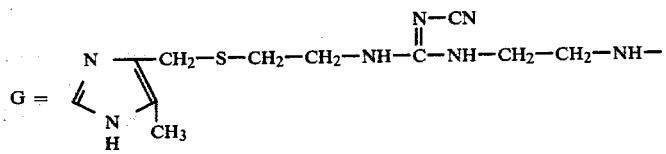

15 grams of N-Cyano-N'-[2-amino-ethyl]-N''-(2-[5-methyl-imidazolyl-(4)-methylthio]-ethyl)-guanidine, 100 ml methanol, 20 ml dimethyl malonate and 0.5 ml of 33% sodium hydroxide solution were stirred for 5 days at room temperature (20° C.). The reaction mixture was evaporated under a vacuum and the residue subjected to a dry column chromatography on silica gel (elution chloroform; ethanol, 90:10). The fraction containing the reaction product was evaporated and the residue (slowly crystallizing oil) crystallized in the evaporation (from a little isopropanol). Yield: 9.5 grams, M.P. 113°–115° C.

The starting substance was prepared as follows:

10 grams of S-methyl-N-cyano-N'-(2-[5-methylimidazolyl-(4)-methylthio]-ethyl)-isothiourea, 100 grams of ethylene diamine and 100 ml of methanol were boiled under reflux with stirring for 2 hours. The solution was then concentrated in vacuo, the residue (a yellow oil) is dissolved in isopropanol and inoculated.

The base which crystallized out on rubbing and stirring was filtered off under suction after 2 hours (33 grams not quite pure). M.P. 126°–128° C. (the maleate prepared with maleic acid in ethanol melts at 151° to 152° C.

The following G-Ac compounds in Table I produced as in Example 1 from 15 grams of N-cyano-N'[2-amino-ethyl]-N''-(2-[5-methyl-imidazolyl-(4)-methylthio]-ethyl)-guanidine and the acid derivative AcB (in the last column in the parentheses in each case there is given the solvent from which the reaction product was recrystallized.

EXAMPLE 14

N-cyano-N'[2-(p-toluenesulphonylamino)-ethyl]-N''-(2-[5-methyl-imidazolyl-(4)-methylthio]-ethyl)-guanidine

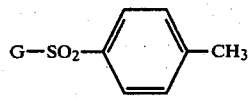

11 grams of p-toluenesulphonic acid chloride was added in portions to a mixture of 15 grams of N-cyano-N'-[2-amino-ethyl]-N''-(2-[5-methyl-imidazolyl-(4)-methylthio]-ethyl)-guanidine in 100 ml of pyridine at room temperature with stirring so that the starting material dissolved. After one hour, the mixture was poured into 1 liter of water shaken with butanol, the butanol extract is shaken once with water, dried and evapo-

TABLE I

| Ex. | Ac | Amount Ac | Deviation from Ex. 1 | Yield | M.P. of the Reaction Product, °C. |
|---|---|---|---|---|---|
| 2 | —CO—CH$_2$CN | 12 grams ethyl cyanoacetate | Reaction time 20 hours;reaction product crystallized out and was recrystallized | 12 grams | 182–184 (from methanol and carbon) |
| 3 | —CO—CF$_3$ | 20 ml ethyl trifluoroacetate | Reaction time 1 hour;solvent ethanol. Evaporation and direct recrystalization of the residue. | 10 grams | 124–126 (from isopropanol) |
| 4 | —CO—CH$_2$F | 20 grams ethyl fluoroacetate | Reaction time 20 hours, reaction product crystallized out and recrystallized | 9 grams | 112–114 (from methanol and carbon) |
| 5 | —CO—CCl$_3$ | 20 ml ethyl trichloroacetate | Reaction time 20 hours, otherwise as Example 2 after inoculation | 11 grams | 124–126 (from ethyl acetate) |
| 6 | —CO—CH—CH$_3$<br>          \|<br>          CN | 18 grams ethyl α-cyanopropionate | Reaction time 6 days;otherwise as Example 2 | 8 grams | 167–169 (from methanol) |
| 7 | —CO—CHCl$_2$ | 20 ml methyl dichloroacetate | Reaction time 24 hours | 14 grams | 146–148 (from ethyl acetate methanol 9:1) |
| 8 | —CH—CH—C$_4$H$_9$<br>      \|<br>      CN | 12 grams methyl α-cyanocaproate | Reaction time 18 days | 7 grams | resin without melting point |
| 9 | —CO—CH(CH$_3$)$_2$<br>      \|<br>      CN | 22 grams methyl α-cyanoisobutyrate | Reaction time 14 days;crystallization of the residue by stirring with ethyl acetate | 3 grams | 120–123 |
| 10 | —CO—CH$_2$—SO—CH$_3$ | 19 grams methyl ester of methyl sulfoxido acetic acid | Reaction time 17 days thorough stirring of the residue with a little alcohol | 8 grams | 108–110 |
| 11 | —CO—CH$_2$—SO$_2$CH$_3$ | 19 grams methyl ester of methyl sulfonyl acetic acid | As in Example 9 | 5.5 grams | 138–140 |
| 12 | —SO$_2$CH$_3$ | 4.8 grams methane sulfonyl chloride | Reaction time 2 hours;200 ml methanol | 1.8 grams | resin |
| 13 | —CO—CH$_2$—COCH$_3$ | 6 ml diketene | Reaction time 24 hours | 8 grams | 142–144 (isopropanol) | rated. The residue, a thick oil was purified by dry column chromatography. The amorphous product was obtained from the fractions containing the desired compound by evaporation and drying. Yield: 2 grams; (no melting point, only slow softening).

EXAMPLE 15

N-cyano-N'-[2-(p-chlorobenzene sulphonylamino)-ethyl]-N''-(2-[5-methyl-imidazolyl-(4)-methylthio]-ethyl)-guanidine

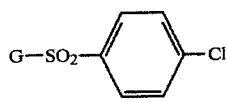

The compound was obtained as in Example 14 using 12.2 grams of p-chlorobenzenesulphonylchloride. Yield: 2 grams. The compound is also amorphous (no definite melting point).

EXAMPLE 16

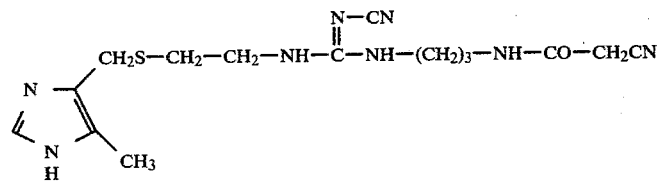

9,2 g N-Cyano-N'-[3-amino-propyl]-N''-(-2-[5-methyl-imidazolyl-(4)-methylthio]-ethyl)-guanidine were stirred in the presence of 0.5 ml 33% sodium hydroxide solution in 500 ml of methanol with 7 grams of ethyl cyanoacetate for 24 hours at 20° C. Then the reaction mixture was evaporated and purified as in the preceding examples by dry column chromatography. The desired fractions were evaporated.

The reaction product is a resin without definite melting point.

Yield: 6 grams.

EXAMPLE 17

N-Cyano-N'[2-trichloracetylamino-ethyl]-N''-[(3-hydroxypyridyl-(2)-methylthio]-ethyl)-guanidine

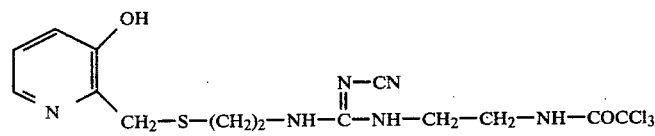

9 grams of N-cyano-N'-[2-aminoethyl]-N''-(2-[3-hydroxypyridyl-(2)-methylthio]-ethyl)-guanidine were reacted with 15 ml of ethyl trichloroacetate in 100 ml of methanol in the presence of 33% of sodium hydroxide solution. After 90 minutes the mixture was evaporated in a vacuum, the residue stirred with ethyl acetate/acetone (9:1) as a result of which slow crystallization took place. It was again, with addition of activated carbon, recrystallized from this mixture.

Yield: 6 grams; M.P. 145°–147° C.

Examples of Pharmaceutical Preparations
Example for Capsules
There are needed to prepare 100,000 capsules:

| I | Material according to Example 1 | 20.0 kg |
|---|---|---|
|  | Microcrystalline cellulose | 10.0 kg |
|  | Lactose | 13.5 kg |
|  | Highly dispersed silica | 0.5 kg |
|  | talc | 1.0 kg |
|  |  | 45.0 kg |
| II | 100,000 gelatin capsules size O | |

Production

All of the raw materials which were needed for the production of the capsule composition were passed through a sieve having a mesh width of 1.5 and subsequently mixed for 1 hour at 10 revolutions per minute in a mixer. The product is a "capsule filling composition".

The capsule filling composition was filled into gelatin capsules of size O.

| Amount of filling composition per capsule | 450 mg |
|---|---|

Example for Film Tablets

There are needed to prepare 100,000 film tablets

| (1) compound according to Example 1 | 20.000 kg |
|---|---|
| (2) Magnesium stearate | 0.125 kg |
| (3) Lactose | 25.000 kg |
| (4) Microcrystalline cellulose | 26.750 kg |
| (5) Corn starch | 4.000 kg |
| (6) Formaldehyde treated casein | 4.000 kg |
| (7) Highly dispersed silica | 0.125 kg |
| weight of the tablets nucleus | 80.000 kg |
| (8) Palmitic acid | 0.225 kg |
| (9) Polywax 6000 | 0.575 kg |
| (10) Titanium dioxide | 0.850 kg |
| (11) Talc | 0.250 kg |
| (12) Polyvinyl pyrrolidone | 0.575 kg |
| (13) Ethyl cellulose | 0.200 kg |
| weight of the film tablets | 82.675 kg |

(A) Production of the Tablets (1) 12.75 kg of microcrystalline cellulose were moistened with 2 liters of demineralized water.

(2) The moistened microcrystalline cellulose was mixed in a suitable mixer with materials 2,5,6 and 7 for 5 minutes.=Mixture 1

(3) Mixture 1 as well as materials 1,3 and the residual amount of microcrystalline cellulose in addition thereto were sieved (sieve 0.8–1 mm mesh width) and homogeneously mixed in a suitable mixer=Mixture 2=Molding composition.

(4) The relative humidity of the Molding composition must be in the range of 45–50%.

(5) The Molding composition was subsequently molded on a rotating pelleting press to curved tablets with the following characteristics:

| | |
|---|---|
| Weight: | 800 mg |
| Diameter: | 12 mm |
| Radius of curvature: | 9 mm |
| Thickness: | 7.2 ± 0.2 mm |
| Hardness: | 7–9 kg (Monsanto Hardness tester) |
| Decomposition time in Cold water: | maximum 2 minutes |

(B) Application of the Film Coating

For the application of a film coating according to the dipping process there are needed for 80 kg of tablets (=100,000 pieces)
15.675 kg=about 13.5 liters of suspension
Composition of the Suspension

| | |
|---|---|
| (1) Isopropanol | 5.000 kg |
| (2) 1,1,1-trichloroethane | 8.000 kg |
| (3) Ethyl cellulose | 0.200 kg |
| (4) Polyvinyl pyrrolidone | 0.575 kg |
| (5) Polywax 6000 | 0.575 kg |
| (6) Palmitic acid | 0.225 kg |
| (7) Titanium dioxide | 0.850 kg |
| (8) Talc | 0.250 kg |
| | 15.675 kg |

Production of the Suspension

Materials 3–6 were dissolved in solvents 1 and 2 which to begin with were heated to 50°–60° C. with stirring=Solution In the cooled Solution there were subsequently homogeneously distributed materials 7 and 8:=Suspension ready for spraying Applying the Tablet Coating in the Dragee (Coating)Kettle To the tablets (80 kg) in the rotating kettle there was applied the suspension as follows:

(a) 1500 ml of suspension were sprayed on (b) Warm air (80° C.) was blown in for about 5 minutes.

This procedure was carried out nine times in succession.

Then the tablets were spread out on lathices and post dried at +45° to +50° C.

The resulting film tablets had a weight of 826.75 mg per tablet. They have a slight luster and offered taste protection for about 15–20 seconds.

EXAMPLE 18

N-Cyano-N'-[2-(carbomethoxyethinylcarbonylamino)-ethyl]-N''-(2-[5-methylimidazolyl-(4)-methylthio]-ethyl)-guanidine

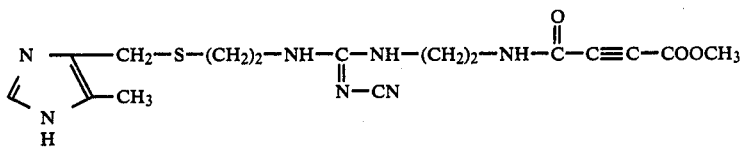

15 grams of N-Cyano-N'-[2-amino-ethyl]-N''-(2-[5-methylimidazolyl-(4)-methylthio]-ethyl)-guanidine, 100 ml of methanol, 6 ml of acetylene dicarboxylic acid dimethyl ester were stirred for 90 minutes at room temperature (20° C.). The reaction mixture was evaporated under a vacuum and the residue subjected to a dry column chromatography or silica gel (elution agent chloroform: ethanol 90.10). The fractions containing the reaction product were evaporated. The initially oily material slowly crystallized; it was then recrystallized from ethanol. Yield: 4 grams; M.P. 144°–146° C.

EXAMPLE 19

N-Cyano-N'-[2-(1-methyl-2,2-dichloro-cyclopropylcarbonyl-amino)-ethyl]-N''-(2-[5-methylimidazolyl-(4)-methylthio]-ethyl)-guanidine

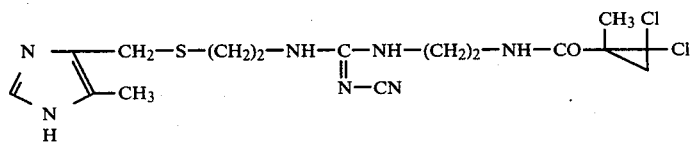

8 grams of 1-methyl-2,2-dichlorocyclopropylcarboxylic acid were dissolved in 80 ml of dioxane and heated with 8 grams of 1,5-carbonyl diimidazole. The mixture was stirred for 30 minutes at room temperature. Then there were added 12 grams of N-Cyano-N'-[2-amino-ethyl]-N''-(2-[5-methylimidazolyl-(4)-methylthio]-ethyl)-guanidine in 80 ml of dimethylformamide and stirring carried out for 2 hours at 20° C. The reaction mixture was evaporated in a vacuum, the residue was purified by dry column chromatography in a manner analogous to that in Example 1. The desired fraction crystallized in triturating with ethyl acetate.

Yield: 9 grams; M.P. 118°–120° C.

EXAMPLE 20

N-Cyano-N'-[2-(1-methyl-cyclopropylcarbonylamino)-ethyl]-N"-(2-[5-methylimidazolyl-(4)-methylthio]-ethyl)-guanidine

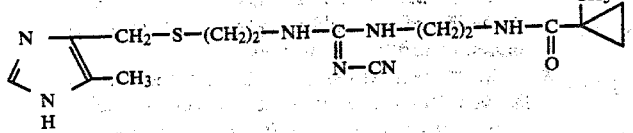

The procedure was analogous to that in example 19 wherein in place of the 1-Methyl-2,2-dichlorocyclopropancarboxylic acid there were added 4.8 grams of 1-methylcyclopropyl carboxylic acid. The desired fraction crystallized after the dry column chromatography in the concentrating. The crystals were washed with ethyl acetate.

Yield: 5.6 grams; M.P. 124°–127° C.

EXAMPLE 21

N-Cyano-N'-[2-(2-methyl-cyclopropylcarbonylamino)-ethyl]-N"-(2-[5-methylimidazolyl-(4)-methylthio]-ethyl)-guanidine.

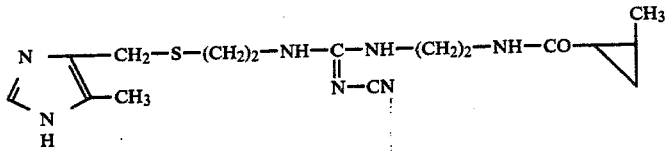

The procedure was analogous to that in Example 20 wherein in place of the 1-methylcyclopropyl carboxylic acid there were added 4.8 grams of 2-methylcyclopropyl carboxylic acid.

Yield: 6.4 grams; M.P. 116°–118° C.

What is claimed is:

1. A compound corresponding to the formula:

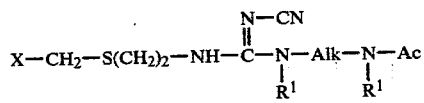

in which X is a imidazolyl, imidazolyl substituted by 1 to 2 $C_1$–$C_4$-alkyl groups, pyridyl or pyridyl substituted in the 3 or 4 position by hydroxy atoms, each $R^1$ represents hydrogen or a $C_1$–$C_4$-alkyl group, Alk represents a $C_2$–$C_6$-alkylene chain and Ac represents a $C_2$–$C_8$-alkanoyl radical or a benzoyl radical substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, sulphamoyl groups, $C_1$–$C_4$-alkylsulphinyl groups or $C_1$–$C_4$-alkylsulphonyl groups, or in which Ac is a cyano group, a formyl group, a $C_2$–$C_6$-alkencarbonyl group, a $C_2$–$C_6$-alkincarbonyl group or such alkenecarbonyl group or alkincarbonyl group substituted by a $C_2$–$C_6$ carbalkoxy group, a $C_3$–$C_6$-cycloalkancarbonyl group or such a group substituted by halogen and/or a $C_1$–$C_6$-alkyl group, or in which Ac is a $C_1$–$C_6$-alkylsulphonyl radical or a phenyl sulphonyl radical in which the alkyl or phenyl moiety may be substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, $C_1$–$C_4$-alkylsulphinyl groups, $C_1$–$C_4$-alkylsulphonyl groups, sulphamoyl groups, hydroxy groups, mercapto groups, $C_1$–$C_4$-alkoxy groups, $C_1$–$C_4$-alkyl mercapto groups or $C_1$–$C_4$-alkyl groups or a salt thereof with a pharmaceutically acceptable acid.

2. A compound according to claim 1 wherein Ac represents a $C_2$–$C_8$-alkanoyl radical or a benzoyl radical respectively substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, sulphamoyl groups, $C_1$–$C_4$-alkylsulphinyl groups or $C_1$–$C_4$-alkylsulphonyl groups, or in which Ac is a formyl group, a $C_2$–$C_6$-alkenecarbonyl group, a $C_2$–$C_6$-alkincarbonyl group or such alkenecarbonyl group or alkinecarbonyl group substituted by a $C_2$–$C_6$ carbalkoxy group, a $C_3$–$C_6$-cycloalkanecarbonyl group or such a group substituted by halogen and/or a $C_1$–$C_6$ alkyl group, or in which Ac is a $C_1$–$C_6$-alkylsulphonyl radical or a phenyl sulphonyl radical in which the alkyl or phenyl moiety may be substituted once, twice or three times by halogen atoms, nitrile groups, nitro groups, carboxy groups, carbamoyl groups, $C_2$–$C_5$-carbalkoxy groups, $C_1$–$C_4$-alkylsulphinyl groups, $C_1$–$C_4$-alkylsulphonyl groups, sulphamoyl groups, hydroxy, mercapto groups, $C_1$–$C_4$-alkoxy groups, $C_1$–$C_4$-alkyl mercapto groups or $C_1$–$C_4$-alkyl groups.

3. A compound according to claim 1 wherein Ac represents a $C_2$–$C_8$-alkanoyl radical or a benzoyl radical respectively substituted once, twice or three times by halogen atoms, nitrile groups, nitro groups, carboxy groups, carbamoyl groups, $C_2$–$C_5$-alkylcarbonyl groups, $C_2$–$C_5$-carbalkoxy groups, sulphamoyl groups, $C_1$–$C_5$-alkylsulphinyl groups or $C_1$–$C_4$-alkylsulphonyl groups, or in which Ac is a $C_1$–$C_6$-alkylsulphonyl radical or a phenyl sulphonyl radical in which the alkyl or phenyl moiety may be substituted once, twice or three times by halogen atoms, nitrile groups, carboxy groups, carbamoyl groups, $C_2$–$C_5$-alkylcarbonyl groups, $C_2$–$C_5$-carbalkoxy groups, $C_1$–$C_4$-alkylsulphinyl groups, $C_1$–$C_4$-alkylsulphonyl groups, sulphamoyl groups, hydroxy groups, mercapto groups, $C_1$–$C_4$-alkoxy groups, $C_1$–$C_4$-alkyl mercapto groups or $C_1$–$C_4$-alkyl groups.

4. A compound according to claim 1 wherein Ac is a $C_2$–$C_8$-alkanoyl group substituted by a $C_2$–$C_5$-carbalkoxy group, a cyano group, 1 to 3 halogen atoms, a $C_1$–$C_4$-alkylsulphinyl group, a $C_1$–$C_4$-alkyl sulphonyl group, a $C_2$–$C_5$-alkylcarbonyl group or Ac is, a lower alkylphenyl sulphonyl radical, or a halophenylsulphonyl radical.

5. A compound according to claim 1 wherein Ac is carbomethyoxyacetyl, cyanoacetyl, trifluoroacetyl, monofluoroacetyl, 2-cyanopropionyl, dichloroacetyl, 2-cyanocaproyl, 2-cyanoisobutyryl, methylsulphinylacetyl, methylsulphonylacetyl, methylsulphonyl, methylcarbonylacetyl, tolylsulphonyl, chlorophenylsulphonyl or trichloroacetyl.

6. A compound according to claim 5 wherein the heterocyclic radical is 5-methylimidazolyl-(4).

7. A compound according to claim 5 where Alk is a $C_2$–$C_3$-alkylene group.

8. A medicament containing as an active ingredient in an amount sufficient to inhibit secretion of stomach acid or to heal ulcers or to provide antihistamine action of the $H_2$-Blocker type a compound of claim 1 together with a pharmaceutical excipient or diluent.

9. A method of combatting ulcers in a mammal comprising administering to the mammal an amount of a compound of claim 1 effective to provide ulcer healing.

10. A method of retarding secretion of stomach secretions in a mammal comprising administering to the mammal an amount of a compound of claim 1 effective to retard said secretion.

11. A method of providing a mammal with an antihistamine or the $H_2$-Blocker type comprising administering to the mammal an amount of a compound of claim 1 effective to provide said antihistamine action.

12. A method of administering the medicament of claim 8 to a mammal comprising administering the medicament orally or parenterally.

13. A compound according to claim 1 wherein Ac is lower alkoxyethinyl carbonyl or is cyclopropyl carbonyl or cyclopropyl carbonyl substituted with at least one lower alkyl or halogen or both lower alkyl and halogen.

14. A compound according to claim 13 in which X is 5-methylimidazolyl-(4) and Ac is methoxycarbonyl ethinyl.

15. A compound according to claim 13 wherein Ac is cyclopropane carbonyl and the cyclopropane carbonyl has 0 to 3 substituents selected from the group consisting of methyl and chloro.

* * * * *